United States Patent [19]

Odrich

[11] Patent Number: 5,000,684

[45] Date of Patent: Mar. 19, 1991

[54] SUPRA AND SUBGINGIVAL TOOTH CLEANING APPARATUS AND METHOD

[76] Inventor: Ronald Odrich, 4710 Livingston Ave., Bronx, N.Y. 10471

[21] Appl. No.: 391,870

[22] Filed: Aug. 10, 1989

[51] Int. Cl.⁵ .................................................. A61C 3/06
[52] U.S. Cl. ..................................... 433/125; 433/127; 433/118; 128/62 A
[58] Field of Search ............... 433/125, 142, 146, 127, 433/147, 166, 103, 118, 124, 128, 141, 126, 215, 216, 165; 132/309, 321, 329; 15/167.1; 128/62 A

[56] References Cited

U.S. PATENT DOCUMENTS

| | | | |
|---|---|---|---|
| 1,086,936 | 2/1914 | Pounder et al. | 128/62 A |
| 2,016,597 | 10/1935 | Drake | 128/62 A |
| 2,134,934 | 11/1938 | Wilhoit | 128/62 A |
| 2,135,933 | 11/1938 | Blair | 433/166 |
| 2,141,969 | 12/1938 | Benz | 128/62 A |
| 3,091,033 | 5/1963 | Ellman | 433/216 |
| 3,720,975 | 3/1975 | Nelson | 15/167.1 |
| 4,371,341 | 2/1983 | Nakanishi | 433/118 |
| 4,880,382 | 11/1989 | Moret et al. | 433/118 |

FOREIGN PATENT DOCUMENTS

| | | | |
|---|---|---|---|
| 64871 | 11/1982 | European Pat. Off. | 433/124 |
| 2209562 | 9/1973 | Fed. Rep. of Germany | 433/166 |
| 333001 | 5/1959 | Switzerland | 15/167.1 |

Primary Examiner—Cary E. Stone
Attorney, Agent, or Firm—Notaro & Michalos

[57] ABSTRACT

An apparatus and method for the supra and subgingival cleaning of teeth comprises and handle with a driving mechanism for reciprocally rotating a tapered cleaning tip about its longitudinal axis. A tuft or other scrubbing mechanism is provided on the outer circumference of the tip. The tip includes circumferentially disposed flutes which can be used to receive and dispense medication to the subgingival area. The tip is introduced into the gap between the gum and the tooth for scrubbing the outer surfaces of the tooth near and under the gum line. This effectively disrupts any bacteria plaque in these areas to clean the tooth.

29 Claims, 5 Drawing Sheets

SUPRA AND SUBGINGIVAL TOOTH CLEANING APPARATUS AND METHOD

FIELD AND BACKGROUND OF THE INVENTION

The present invention relates in general to equipment and techniques for cleaning the surfaces of teeth, and in particular, to a new and useful apparatus and method of cleaning the supragingival and subgingival surfaces of teeth.

The elimination of bacterial plaque from crown and root surfaces of teeth is essential for the prevention and treatment of periodontal disease. Despite the existence of a wide variety of oral hygiene aids, none is completely effective in eliminating dental plaque, particularly from subgingival surfaces of the teeth. Manual tooth brushing can only detach plaque from areas of the teeth which are at or above the gum line, and only on the facial and lingual surfaces of the teeth. While dental floss can be used to remove plaque from interproximal surfaces, that is surfaces between the teeth, dental floss is difficult to use and is only capable of reaching to a shallow depth below the gum line.

Another device which is known by the tradename PERIO-AID and shown in U.S. Pat. No. 3,892,040, has been useful in removing plaque from subgingival or root surfaces of teeth. The PERIO-AID comprises a plastic handle into which a pair of toothpicks having round cross-sections can be inserted. The toothpicks extend at different angles so that at least one toothpick is at a convenient angle for use in cleaning the teeth subgingivally. Problems in using this device include the fact that the material and dimensions of toothpicks vary. It is sometimes difficult to locate toothpicks of the correct cross-section, strength and dimension for use with the PERIO-AID device. During use the toothpicks tend to break. In addition, it is difficult to correctly angle and move the handle for proper cleaning of the subgingival surfaces.

Another available tooth cleaning device marketed under the name INTERPLAK utilizes a plurality of reciprocally rotating bristle tufts which are distributed in a pattern reminiscent of a conventional toothbrush. The bristles are rotated through a number of turns in one direction and then through a number of turns in an opposite direction by an electrically powered mechanism. A mechanical reciprocating mechanism of this type is disclosed in U.S. Pat. No. 4,156,620. The average gingival sulcus in humans is one to three millimeters deep. The action of the tufts of the INTERPLAK device is not capable of significantly penetrating into the gingival crevice (sulcus) enough to clean off the plaque. There certainly is no likelihood that the tufts of the INTERPLAK device could reach or remove the plaque in deeper periodontal pockets which can range from four to twelve millimeters in depth.

As disclosed in U.S. Pat. No. 4,156,620, the bristles of each tuft extend parallel to the longitudinal axis of the tuft. During rotation in one direction, the effective length of the bristles shortens as the bristle are twisted about the axis of the tuft. Upon rotating the tuft in an opposite direction, the effective length of the bristles increases. This helps force the bristles against interproximal surfaces of the teeth for cleaning between the teeth. This action has limited effectiveness on the subgingival surfaces of the teeth, however.

Plaque which grows near and below the gum line, is the very plaque which causes periodontal disease. Subgingival plaque is a stratified mat of highly organized bacteria. Unlike supragingival plaque, however, subgingival plaque is less adherent to the subgingival root surfaces of the teeth. Even gentle disruption of the subgingival plaque is thus capable of disrupting its organization and preventing its maturation. Disrupting subgingival plaque, however, requires access into the gingival sulcus and into even deeper periodontal pockets and proper movement of an appropriate device once access is achieved.

Nothing is available today which can achieve this action.

The need thus remains for an apparatus or technique which is capable of effective subgingival removal of bacterial plaque. Such an apparatus or method should be capable of cleaning root surfaces in periodontal pockets as well.

SUMMARY OF THE INVENTION

The present invention comprises an apparatus and method for the supra and subgingival cleaning of teeth utilizing a reciprocally rotating tapered tip or tool carrying circumferentially spaced and radially active scrubbing means which are capable of disrupting and cleaning plaque from gingival surfaces of the tooth crown and subgingival surfaces of the tooth root. The tip advantageously tapers to a small ball or point which is helpful in introducing the tip between the gum and the tooth. A tuft which is made of fibers or other structures may act as the scrub- bing means. Alternatively, or in addition to the tuft, the tip may have a polygonal cross-section with the corners of the polygon acting to scrub the tooth surfaces. The tip includes longitudinally extending flutes which can be used for receiving and dispensing anti-plaque material or other medication which is in liquid, paste or gel form. The penetrating action of the tip helps distribute this material to the areas where it is most needed.

The reciprocal rotary motion of the tip may be achieved using a rack and pinion gear arrangement driven by an electric motor of electric solenoid. Alternatively, hydraulic or pneumatic fluid can be used to drive a fluidic oscillator and fluid driven motor for achieving the reciprocal rotation of the tip. Alternatively, the tip may be vibrated to achieve plaque disruption.

The tip is advantageously made of pliable plastic both for ease of manufacture and to avoid damage to the gum tissues.

Currently, the treatment for deep periodontal pockets is one or another type of surgical procedure. The rationale for surgical reduction of pockets is to create access for the patient to facilitate daily plaque removal from root surfaces previously separated from their gingival attachments by bouts of periodontal disease activity.

An instrument which permits plaque removal without resorting to surgical intervention is of great value in the treatment and prevention of periodontal disease. Periodontal pockets and bone loss are most prevalent in areas between the teeth. Bone loss and pockets form with great frequency between the roots of multi-rooted teeth (bifurcation and trifurcation detachments). In such instances there is currently no means available to remove plaque in these areas. The mechanically activated tip of the present invention makes plaque removal possible in these areas.

The tip of the invention can reach deep periodontal pockets and is useful during all phases of periodontal treatment. An individual can use the invention during daily oral hygiene procedures for removing plaque at and below the gum and 360° around each tooth for healthy gingival sulci. One embodiment of the tip is designed especially for removing plaque from the supra and subgingival surfaces of the part of dental implants which extend into the oral cavity.

The tip may even be used alone or on a non-mechanical handle that simply holds the tip. Proper scrubbing action in this case is supplied by the user.

Accordingly, one object of the present invention is to provide an apparatus for supragingival and subgingival cleaning of teeth which comprises a handle, an elongated tapered cleaning tip having an axis and mounted for reciprocal rotary motion to the handle about the axis, with an outer surface of the tip including circumferentially spaced radially active scrubbing means for scrubbing supragingival and subgingival surfaces of a tooth, and drive means connected to the tip for reciprocally rotating the tip.

A further object of the present invention is to provide a method for cleaning the supragingival and subgingival surfaces of teeth which comprises engaging the side of a tapered cleaning tip having circumferentially spaced radially active scrubbing means, against the supragingival and subgingival surfaces of a tooth and reciprocally rotating the tip around its axis for scrubbing the surfaces of the tooth.

A still further object of the invention is to provide a tip which can be used to clean the supra and subgingival surfaces of teeth.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which the preferred embodiments of the invention are illustrated.

DESCRIPTION OF THE PREFERRED EMBODIMENTS

Figures 1, 2:
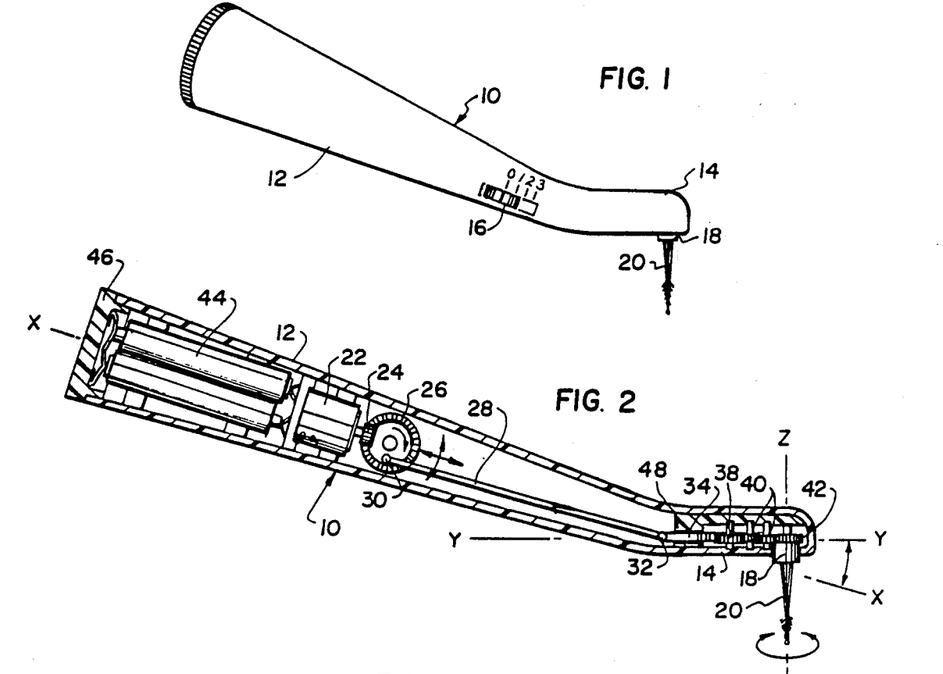
FIG. 1 is a perspective view of one embodiment of the apparatus for cleaning the supragingival and subgingival surfaces of teeth in accordance with the present invention.
FIG. 2 is a sectional view through the apparatus of FIG. 1.

Referring to the drawings in particular, the invention embodied in FIGS. 1 and 2 comprises a hand held apparatus generally designated 10 for use in the cleaning of supra and subgingival surfaces of the teeth. Apparatus 10 comprises a handle housing in the form of a closed shell having a handle portion 12 connected congruently with a head portion 14. As best shown in FIG. 2, the axis X-X of handle portion 12 extends at an angle to the axis Y-Y of the head portion 14. While this angle is preferably from 15° to 45°, angle 13 may be anywhere from 0° to 90°.

The housing of apparatus 10 encloses drive means and a power source for reciprocally rotating a chuck 18 which is mounted for rotation on an axis Z-Z to the head portion 14. Rotation axis Z-Z is advantageously perpendicular to head portion axis Y-Y.

A four position slide switch 16 is mounted on one side of the handle housing for use in activating the drive mechanism in the housing.

Figure 3:
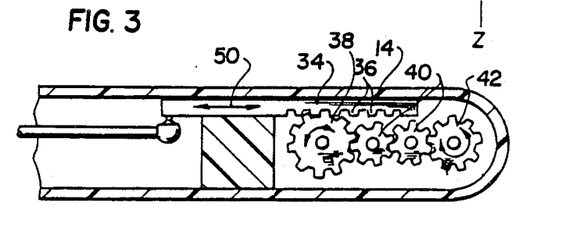
FIG. 3 is a partial sectional view showing the mechanical drive of the embodiment of FIG. 2.

A cleaning tip or tool 20 is detachably connected to chuck 18 and subjected to the reciprocal rotary motion of the chuck. As best shown in FIGS. 2 and 3, the drive means for chuck 18 comprise a small battery driven motor 22 having a pinion gear 24 meshed with a crown gear 26 which is mounted for rotation in the housing. A crank 28 is mounted for rotation to the crown gear 26 at a location 30 which is eccentric with respect to the rotation axis of the crown gear. The opposite end of crank 28 is connected at a universal ball joint 32 to a rack shaft 34 which carries a row of rack teeth 36 that are meshed with a pinion gear 38 mounted for rotation about an axis parallel to the tip axis Z-Z, in head portion 14 of the handle housing.

Rotation of gear 38 is transmitted and increased over intermediate gears 40 to a chuck gear 42 which is fixed to chuck 18. A pair of small (e.g. AAA) DC batteries 44 are contained within a compartment in the handle portion 12 which is covered by a removable end cap 46.

The utilization of space within the housing shell is maximized by providing the shell with an oval cross-section having a major axis extending in the plane of FIG. 2.

Insulating low friction material encloses rotation shafts for the pinions and forms a linear slide bearing 48 for the rack shaft in head portion 14, for the free movement of these parts.

Figure 4:
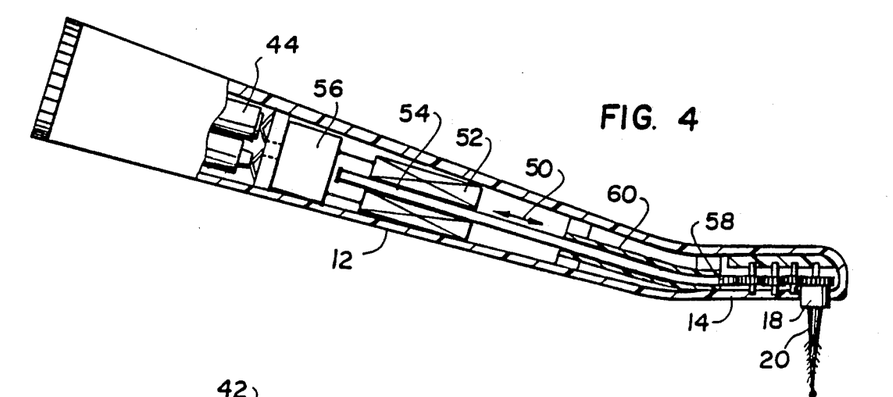
FIG. 4 is a view similar to FIG. 2 of a second embodiment of the invention.

Batteries 44 are connected through switch 16 to motor 22 for powering the motor. This rotates pinion gear 24 which in turn causes rotation of crown gear 26 and a rotary pushing and pulling action on crank 28. This action is transferred to a pushing and pulling action on the rack shaft 34 which is held for linear motion in the linear bearing 48 fixed in the handle housing. The dimensions and gear ratios for the drive train between the motor 22 and the chuck gear 42 is selected so that with the reciprocal movement of rack shaft 34 in a direction of arrow 50, chuck 18 makes anywhere from one-quarter to one full turn in one direction and then rotates an equal amount in the opposite direction. The multiple positions for slide 16 correspond to different speeds for the rotary reciprocal movement and/or different amplitudes (amounts of rotation) for that movement. To facilitate the more convenient selection of multiple amplitudes, the embodiment of FIG. 4 utilizes a solenoid coil 52 which has a sliding part 54 containing a magnet core. An oscillator circuit 56 is connected to batteries 44 and switch 16 to provide alternating current to coil 42. According to a selected timing, the alternating current causes reciprocal movement of magnetic core part 54 which is transmitted to a rack shaft 58 meshed with a gear train identical to that shown in FIG. 3 for reciprocally rotating the chuck 18. To simplify and reduce the number of mechanical parts required. Core part 54 and shaft 58 are made of a single piece of flexible material which is curved gently in a rigid tube-like linear bearing 60 which accommodates for the angle between the handle portion 12 and the head portion 14. Advantageously circuit 56 is designed so that with slide switch 16 in a position 1 shown in FIG. 1, shaft 54, 58 moves sufficiently to rotate chuck 18° to 90° (one-quarter turn) in one direction, and then 90° in the opposite direction. With switch 16 in position 2, chuck 18 rotates 180° (one-half turn) in one direction, and then 180° in the opposite direction. With switch 16 in position 3, chuck 18 rotates 360° (one full turn) in one direction, and then 360° in the opposite direction.

In this way, three distinct settings corresponding to three rotary strokes for the cleaning tip can be selected.

The field of solenoids and circuits to drive them is sufficiently developed so that the person with ordinary skill in that field can design the correct drive for this invention.

Figures 5, 6:
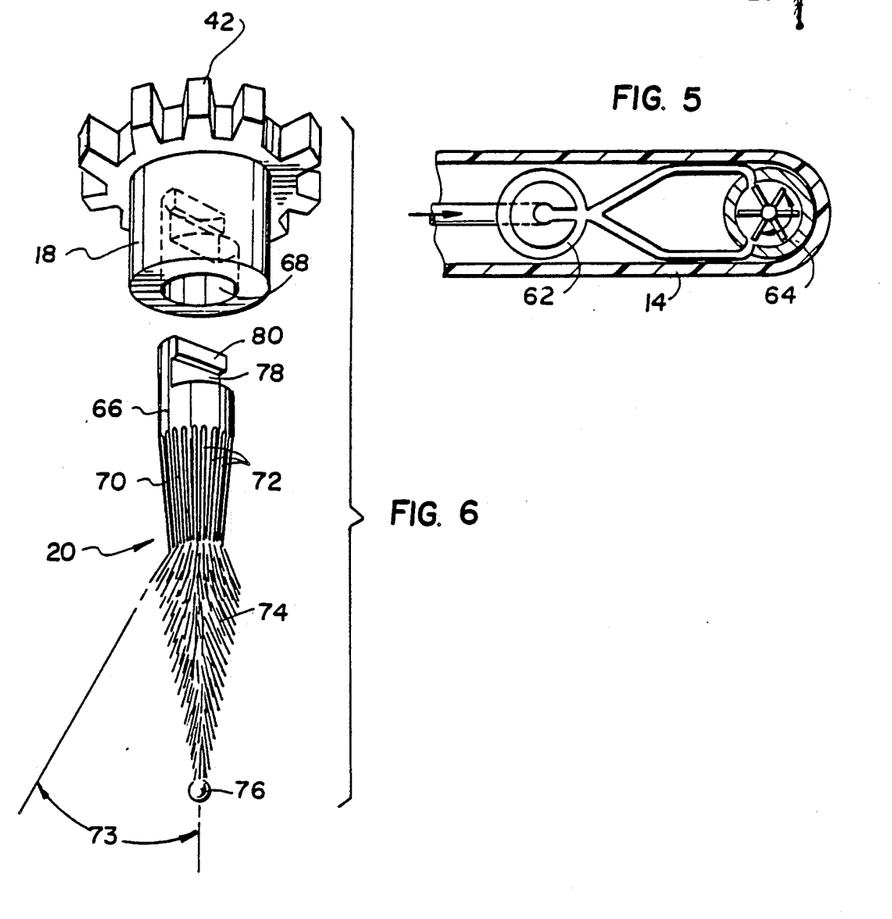
FIG. 5 is a view similar to FIG. 3 of an alternate drive for the present invention.
FIG. 6 is a perspective exploded view of a tip and engagement means for engaging the tip to the handle of the present invention.

FIG. 5 shows a further embodiment of the invention which is driven by hydraulic or pneumatic fluid rather than by electricity. As with the other figures in the drawings, the same reference numerals are utilized to designate the same or similar parts. In FIG. 5, head portion 14 contains a fluidic oscillator 62 of conventional design which is connected to the forward and reverse ports of a reversible hydraulic or pneumatic motor 64. Chuck 18 (not shown in FIG. 5) is connected directly to the output shaft of motor 64. The amplitude and frequency of rotary motion for the cleaning tool in the embodiment of FIG. 5 can be adjusted by regulating the pressure of the fluid medium and/or by pulsing the fluid medium.

The active element of the invention is the cleaning tip whose reciprocal rotary motion can be used to cleanse away plaque from supra and subgingival surfaces of the tooth.

FIGS. 6–11 illustrate various embodiments of the tip.

In FIG. 6, tip 20 comprises a one piece plastic structure made of flexible resilient material. The tip includes a handle engagement end 66 which is shaped for engagement into a mating socket 68 in the chuck 18, for co-rotation of the chuck and tip. A tapered shank 70 having circumferentially spaced axially extending flutes 72 which are shaped for receiving and distributing antiplaque or other medication, is connected to end 66. A tuft of fibers 74 is formed at the small insertion end of tapered shank 70. A small diameter spherical ball 76 is provided at the end of tapered shank 70. The fibers of tuft 74 are made of the same material as the remainder of the tip 20 and advantageously extend at an angle 73 of from 15° to 90° from the axis Z-Z of tip 20. Preferably, this angle is 30° to 60°.

The tuft 74 and, to some extents, the flutes of tapered shaft 70, act as circumferentially spaced radially active scrubbing means for scrubbing supra and subgingival tooth surfaces.

To insure firm engagement between the end 66 of the tip and the chuck 18, end 66 has a flat area 78 which terminates in a raised step 80. These structures match a surface and recess in socket 68. Being made of resilient material, step 80 is resiliently squeezed to admit end 66 into socket 68. Step 80 then expands into the recess in socket 68 to hold the tip firmly in the chuck 18.

Figure 7:
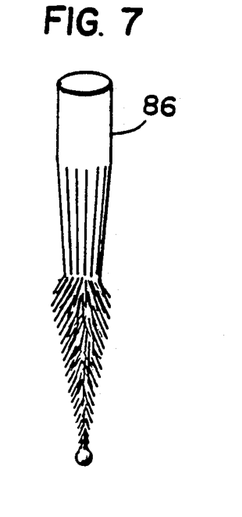
FIG. 7 is a perspective view showing an alternate embodiment of the tip.

FIG. 7 shows an alternate embodiment of the tip which includes a cylindrical end 86 for engagement into a cylindrical hole in a chuck (not shown) designed to receive the tip end. FIG. 7 also shows a large size for tip which typically has a shank length of approximately one inch with a tuft occupying approximately one-quarter to three-quarters of the shank. The tip can be supplied in long, medium or small lengths for different dental needs.

Figure 8:
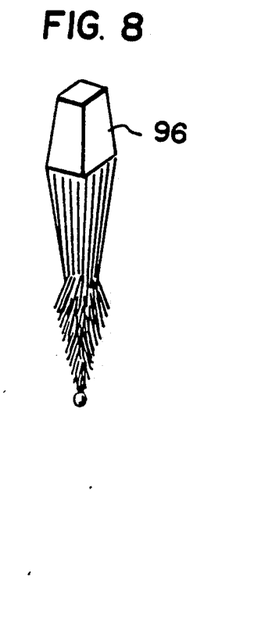
FIG. 8 is a view similar to FIG. 7 showing a further embodiment of the tip.

FIG. 8 shows a further embodiment of the invention having engagement end 96 in the form of a tapered polygon which can be wedged into a correspondingly shaped socket in a chuck.

Figure 9:
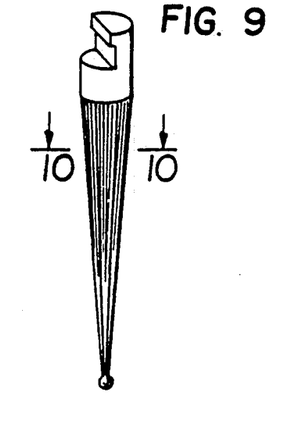
FIG. 9 is a view similar to FIG. 8 showing a still further embodiment of the invention.
Figure 10:
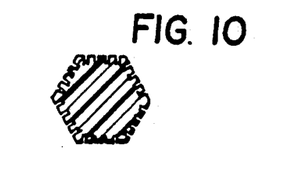
FIG. 10 is a sectional view taken along line 10-10 of FIG. 9.

FIG. 9 and 10 show an embodiment of the invention which has a shank with a polygonal cross-section having circumferentially spaced flutes but no tuft. In this embodiment, the corners of the polygon act as the circumferentially spaced scrubbing means.

Figure 9A:
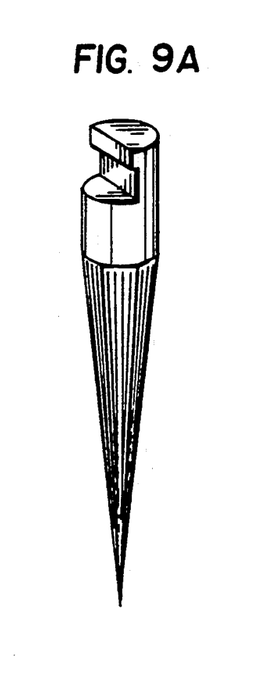
FIG. 9A is a view similar to FIG. 9 of another embodiment of the tip.

FIG. 9A shows an embodiment of the invention having a tapered shank which tapers to a pointed insertion end having no ball structure.

Figure 9B:
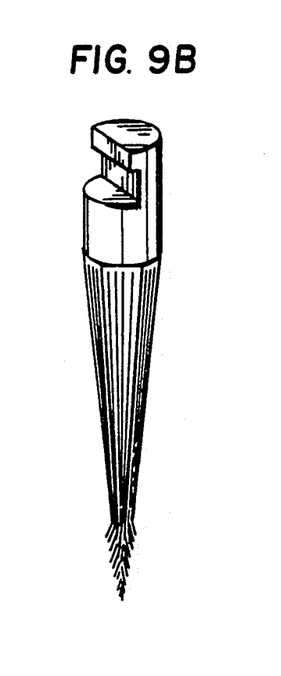
FIG. 9B is a view similar to FIG. 9 of a further embodiment of the tip.

FIG. 9B is a version similar to that of FIG. 9 but including a tuft of fibers only at the very end of the shank.

Figure 9C:
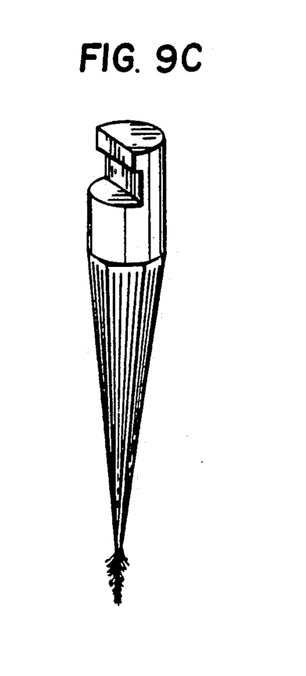
FIG. 9C is a view similar to FIG. 9 of a still further embodiment of the tip.

FIG. 9C is an embodiment of the invention similar to that of FIG. 9B but with a thinner cross section to the shank near the insertion end and only a few fibers in the tuft.

Typical diameters for the handle insertion end are from 1mm to 5mm with a preferred range being from 1.5mm to 3mm. The examples shown in the figures have a handle engagement end diameter of 2mm. The axially length of the engagement end is 4mm. A typical range is 1mm to 10mm with a preferred range being 3mm to 5mm.

The axial length of the tapered shank which forms the working portion of the tip is preferably 19mm for a long tip, 16mm for a medium and 10mm for a short tip. Typical tips are from 7mm to 3.7cm in length with a preferred length of 10mm to 2.5 cm.

The taper of the tapered shank is preferably 5° to the axis of the tip with a usable range of 0° to 45°. Preferred limits for the taper are, however, 3° to 10°. The diameter of the ball at the end of the tip may be 0mm (for the pointed insertion end) to 1.5mm. The tufts in the embodiment of the tips having tufts, are made of soft fine bristles similar to those found in a fine paint brush. They can be formed by simply fraying the end of the tapered shank.

Figure 11:
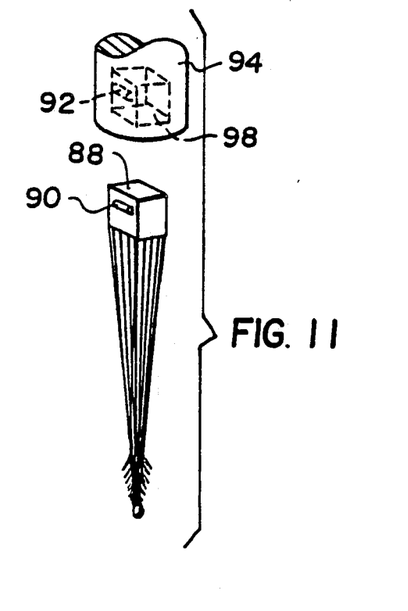
FIG. 11 is an exploded perspective view similar to FIG. 6 of another embodiment of the tip and mechanism for engaging the tip to a handle.

FIG. 11 shows an embodiment of the invention having an engagement end 88 which is polygonal in shape but not tapered. A projection 90 is formed on one side of end 88 which extends into a recess 92 in a socket 98 for receiving the end 88. Socket 98 is formed in a chuck 94 which is otherwise similar to chuck 18 in FIG. 6.

FIG. 11 also illustrates a shank of the type which is useful in cleaning dental implants. For this purpose, the tuft occupies only about one-quarter of a shank length.

Figure 12:
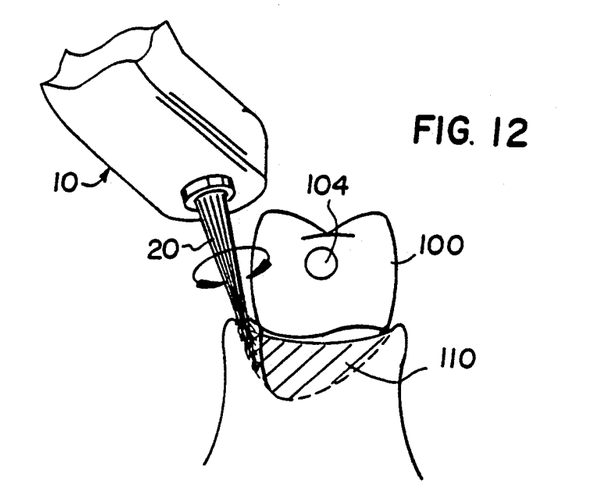
FIG. 12 is a schematic view showing the interproximal surface of a tooth and gingiva to be cleaned by the present invention.
Figure 13:
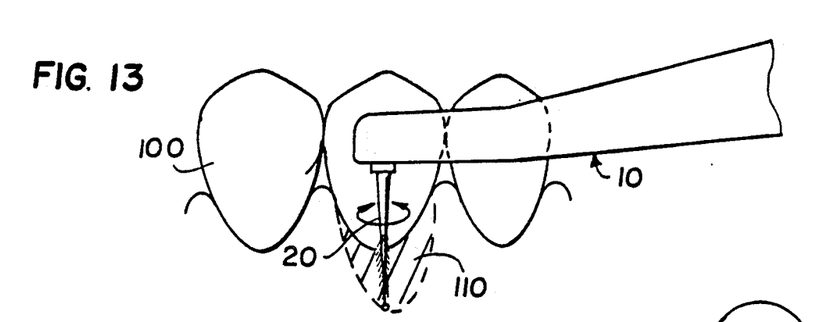
FIG. 13 is a schematic facial view of a tooth to be cleaned with the present invention.
Figure 14:
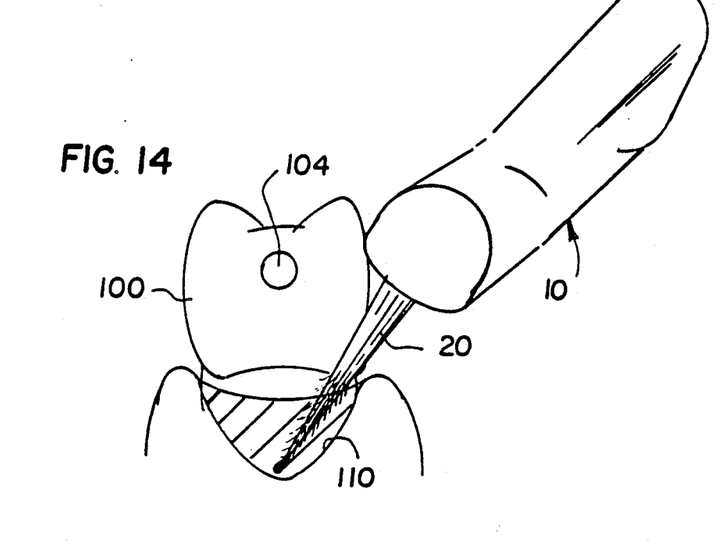
FIG. 14 is a view similar to FIG. 12 showing the cleaning of subgingival interproximal surfaces in accordance with the present invention.

The technique for using the apparatus of the present invention is illustrated in FIGS. 12 to 14.

As shown in FIG. 12, the tip can be introduced into the gingival gap or sulcus on the facial side of a tooth 100. In FIG. 12 the lingual side is to the right. Area 104 is the contact area with an adjacent tooth and 110 is a pocket.

As shown in FIG. 13, tip 20 can reach deeply into a periodontal pocket 110 for cleaning the supra and subgingival surfaces of the tooth. A similar action can be used for cleaning the lingual sulcus.

As shown in FIG. 14, tip 20 can be introduced into any interproximal pockets for cleaning supra and subgingival interproximal surfaces of the tooth. The diameter and length of the cleaning tip 20 is selected so that it can fit between teeth almost up to the contact region 104.

Even more effective cleaning can be achieved by dipping the tip into anti-plaque or other liquid, paste or gel medications. The flutes in the tip help retain the medication until it can be deposited onto the tooth surfaces by the rotation and scrubbing action of the tip. The spherical ball at the end of the tip is provided to avoid damage to the gingival.

Instead of a tuft of fibers, the end of the tip may be provided with a rough textured surface to achieve the same scrubbing action. In the embodiment of the invention using hydraulic (e.g. water) or pneumatic power, an outlet opening can be provided in the housing near the head portion 14 for discharging the fluid into the area being cleaned by the tip. In this way, the fluid is used both to drive the tip and to irrigate the area being cleaned.

The tip with flutes but no tuft can also clean away plaque. In this form of the invention the flutes act as the scrubbing means.

Figure 15:
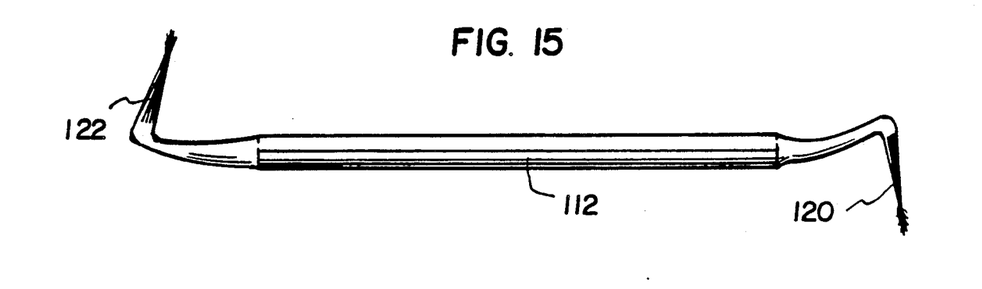
FIG. 15 is a side view of a handle with tips used with a manual cleaning action according to the invention.

FIG. 15 shows an embodiment of the invention having a non-mechanical handle 112 with a tip 120 and 122 connected at either end. Advantageously, the handle and tips are made of a single piece of plastic with sufficient rigidity to provide strength in the handle and sufficient resiliency to provide flexibility in the tips. The tips include tapered shanks with flutes and other structures similar to those that are shown in the embodiments of FIGS. 6-11. Tips 120 and 122 are disposed at different angles with respect to the axis of the handle 112 so that at least one of the tips will be at a convenient angle for insertion between the tooth surface and gum. Scrubbing action for tips 120 and 122 must be provided manually by the user.

While specific embodiments of the invention have been shown and described in detail to illustrate the application of the principles of the invention, it will be understood that the invention may be embodied otherwise without departing from such principles.

What is claimed is:

1. An apparatus for the subgingival cleaning of teeth comprising:
   a handle;
   an elongated tapered non-metallic cleaning tip having an axis and mounted for reciprocal rotary motion to said handle about said axis, said tip having an outer surface including circumferentially spaced radially active scrubbing means for scrubbing subgingival surfaces of a tooth, said cleaning tip including a tapered shank, said scrubbing means comprising a tuft of fibers connected near an end of said shank; and
   drive means connected to said tip for reciprocally rotating said tip about its axis, said drive means rotating said tip by from one quarter to one full turn in either rotary direction.

2. An apparatus according to claim 1, wherein said tip has a polygonal cross-section.

3. An apparatus according to claim 1, wherein said tuft comprises a multiplicity of fibers extending at an angle from 15° to 90° with respect to said axis.

4. An apparatus according to claim 1, including detachable connecting means between said cleaning tip and said drive means for detachable connecting said tip to said handle.

5. A tip for the subgingival cleaning of teeth comprising:
   a one piece non-metallic member having a handle engagement end, a tapered shank connected to said handle engagement end and tapering toward a small diameter insertion end, and circumferentially spaced radially active scrubbing means for scrubbing subgingival surfaces of a tooth, said scrubbing means comprising a tuft of fibers connected to said tapered shank extending at least to said insertion end, said tapered shank has a length of from 7mm to 37mm and a taper angle of from 0° to 45°, said handle engagement end having a diameter of from 1mm to 5mm.

6. A tip according to claim 5 wherein said scrubbing means comprises a plurality of circumferentially spaced axially extending flutes in said tapered shank.

7. A tip according to claim 6 including a ball at said insertion end.

8. A tip according to claim 5 including a handle fixed to and formed as one part with said handle engagement end for holding said tip.

9. A tip according to claim 8 wherein said tapered shank extends at a selected angle to said handle.

10. A tip according to claim 5 wherein said tapered shank has a length of from 10mm to 25mm, the taper angle of said tapered shank being from 3° to 10° and said handle engagement end having a diameter of from 3mm to 5mm.

11. An apparatus for the subgingival cleaning of teeth comprising:
   a handle;
   an elongated tapered non-metallic cleaning tip having an axis and mounted for reciprocal rotary motion to said handle about said axis, said tip having an outer surface including circumferentially spaced radially active scrubbing means for scrubbing subgingival surfaces of a tooth, said cleaning tip including a tapered shank, said scrubbing means comprising a tuft of fibers connected near an end of said shank, said tapered cleaning tip having a spherical end; and drive means connected to said tip for reciprocally rotating said tip about its axis.--

12. An apparatus according to claim 11, wherein said drive means rotates said tip by less than one full turn in either direction.

13. An apparatus according to claim 11, wherein said tapered cleaning tip is conical and includes circumferentially spaced flutes therein above the tuft.

14. An apparatus according to claim 13 wherein said tip comprises a one-piece resilient plastic member.

15. An apparatus according to claim 11, wherein the tip has a length of from 10mm to 25mm, the tip having a taper angle of between 3° and 10°, the maximum diameter of the tip being 3mm to 5mm.

16. An apparatus for the subgingival cleaning of teeth comprising:
   a handle;
   an elongated tapered non-metallic cleaning tip having an axis and mounted for reciprocal rotary motion to said handle about said axis, said tip having an outer surface including circumferentially spaced radially active scrubbing means for scrubbing subgingival surfaces of a tooth, said cleaning tip including a tapered shank, said scrubbing means comprising a tuft of fibers connected near an end of said shank, the tip having a length of from 10mm to 25mm, the tip having a taper angle of between 3° and 10°, the maximum diameter of the top being 3mm to 5mm; and
   drive means connected to said tip for reciprocally rotating said tip about its axis.

17. An apparatus according to claim 16, wherein said tip has a polygonal cross-section.

18. An apparatus according to claim 16, wherein said tuft comprises a multiplicity of fibers extending at an angle from 15° to 90° with respect to said axis.

19. An apparatus according to claim 16, including detachable connecting means between said cleaning tip and said drive means for detachable connecting said tip to said handle.

20. An apparatus according to claim 16, wherein said handle comprises a handle portion having an elongated axis and a head portion connected to said handle portion for carrying said tip, said handle portion extending at an angle of from 0° to 90° with respect to said head portion.

21. An apparatus according to claim 20, wherein said angle is from 15° to 45°.

22. An apparatus according to claim 20, wherein said angle is from 15° to 45°.

23. An apparatus according to claim 16, wherein said handle comprises a handle portion having an elongated axis and a head portion connected to said handle portion for carrying said tip, said handle portion extending at an angle of from 0° to 90° with respect to said head portion.

24. A method for the supra and subgingival cleaning of teeth, comprising:
   engaging the side of a tapered non-metallic cleaning tip having circumferentially spaced radially active scrubbing means, against subgingival surfaces of a tooth; and
   reciprocally rotating said tip about a longitudinal axis thereof by one quarter to one full turn in either direction.

25. A method according to claim 24, including a tuft at an end of said tip forming said scrubbing means.

26. A method according to claim 25, including circumferentially spaced axially extending flutes on an outer surface of said tip for carrying fluid.

27. A method according to claim 26, wherein said tip has a spherical ball shaped end.

28. A method according to claim 24, wherein said tip has a plurality of circumferentially spaced axially extending flutes therein and including dipping the tip into fluid medicinal material before engaging said tip against the supra and subgingival surfaces of the tooth.

29. A method according to claim 24, wherein the tip has a polygonal cross-section, corners of the polygon forming the scrubbing means.

* * * * *